(12) United States Patent
Glock

(10) Patent No.: US 6,962,894 B1
(45) Date of Patent: Nov. 8, 2005

(54) HERBICIDAL COMPOSITION

(75) Inventor: Jutta Glock, Mumpf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 54 days.

(21) Appl. No.: 10/070,766

(22) PCT Filed: Sep. 5, 2000

(86) PCT No.: PCT/EP00/08661

§ 371 (c)(1),
(2), (4) Date: May 31, 2002

(87) PCT Pub. No.: WO01/17353

PCT Pub. Date: Mar. 15, 2001

(30) Foreign Application Priority Data

Sep. 7, 1999 (CH) .............................................. 1643/99

(51) Int. Cl.[7] ...................... A01N 43/56; A61K 31/415; C07D 237/26

(52) U.S. Cl. ..................... 504/238; 504/284; 504/299; 514/405; 514/413; 514/462; 544/238; 548/453; 549/265

(58) Field of Search ................................. 504/238, 284, 504/299, 282; 514/405, 413, 462, 404, 461, 464, 471, 473; 544/235; 548/453, 363.1; 549/265

(56) References Cited

U.S. PATENT DOCUMENTS 5,683,965 A * 11/1997 Bachmann et al. ......... 504/238
6,221,810 B1 * 4/2001 Kruger et al. .............. 504/282

FOREIGN PATENT DOCUMENTS

| WO | WO 96 11574 | 4/1996 |
| WO | WO 96 21652 | 7/1996 |
| WO | WO 98 13361 | 4/1998 |
| WO | WO 99 47525 | 9/1999 |
| WO | WO 00 47585 | 8/2000 |

OTHER PUBLICATIONS

Devine, Malcolm et al., Physiology of Herbicide Action, 1993, PTR Prentice Hall, pp. 376–395.*

* cited by examiner

Primary Examiner—Sabiha N. Qazi
(74) Attorney, Agent, or Firm—Rose M. Allen

(57) ABSTRACT

A selectively herbicidal composition for controlling grasses and weeds in crops of useful plants, comprising
a) a herbicidally effective amount of a compound of formula I

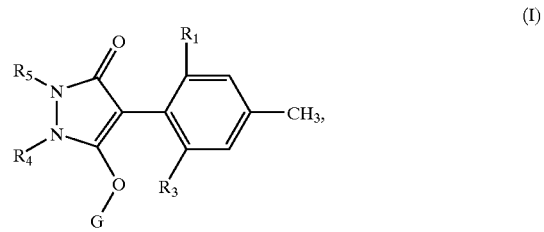

or a salt or diastereoisomer of a compound of formula I, and
b) an amount, which is effective for antagonism of the herbicide, of a compound of formula IIa

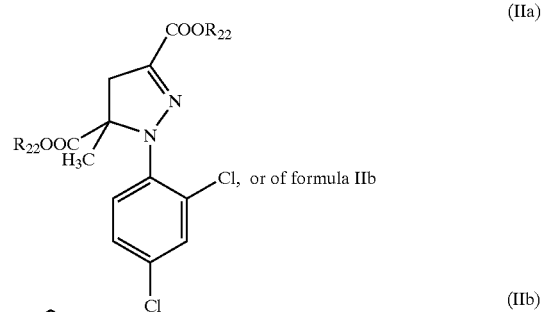

Cl, or of formula IIb

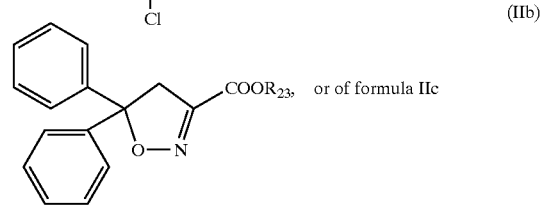

or of formula IIc

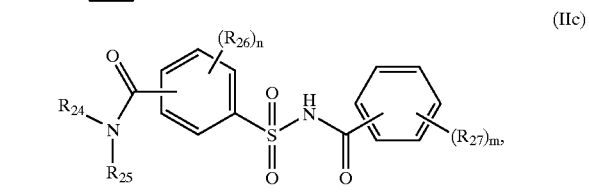

or of formula IId

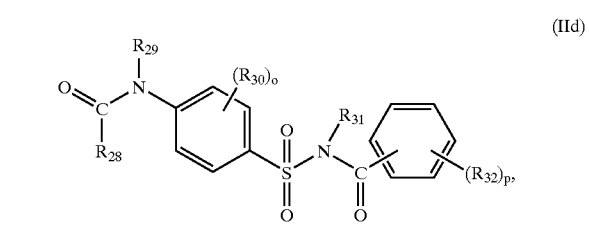

or of formula IIe

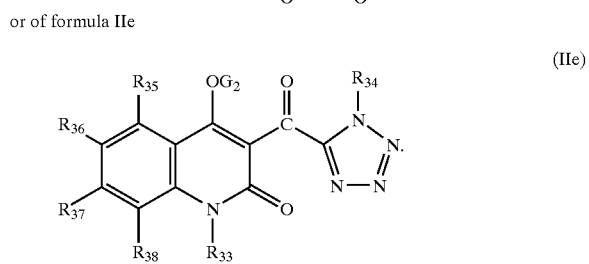

11 Claims, No Drawings

HERBICIDAL COMPOSITION

The present invention relates to new selectively herbicidal compositions for controlling grasses and weeds in crops of useful plants, especially in crops of cereals, maize and sorghum, which compositions comprise a herbicide and a safener (counter-agent, antidote) and protect the useful plants, but not the weeds, against the phytotoxic action of the herbicide, and also to the use of the compositions for controlling weeds in crops of useful plants.

When using herbicides, the cultivated plants may also suffer considerable damage, depending on, for example, the amount of herbicide and the method of application, the species of cultivated plant, the nature of the soil and climatic conditions, for example hours of daylight, temperature and amounts of rainfall. In order to deal with that and similar problems, various substances have already been proposed as safeners, which are capable of antagonising the harmful effect of the herbicide on the cultivated plant, that is to say are capable of protecting the cultivated plant, without appreciably impairing the herbicidal action on the weeds to be controlled. It has been found that the proposed safeners often act very specifically both with respect to the cultivated plants and with respect to the herbicide, and in some cases also in dependence on the method of application, that is to say, a particular safener is often suitable only for a particular cultivated plant and a specific class of herbicidal substance or a particular herbicide. For example, WO 96/21652 and WO 99/47525 disclose compounds that protect the cultivated plants from the phytotoxic action of herbicides such as, for example, 3-hydroxy-4-aryl-5-oxopyrazoline derivatives.

It has now been found that compounds of formula IIa

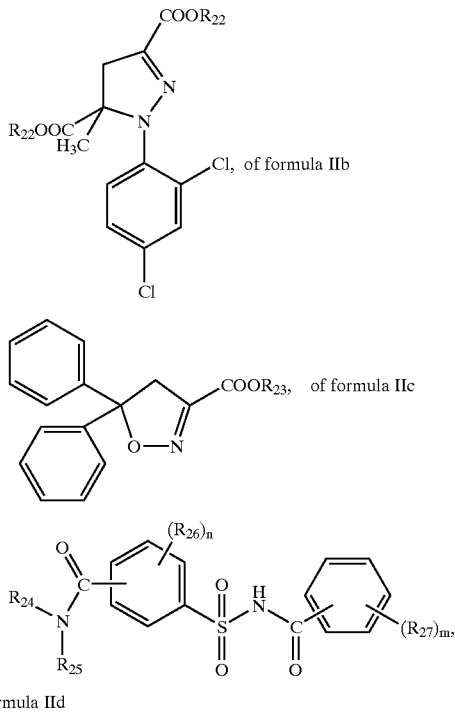

of formula IId

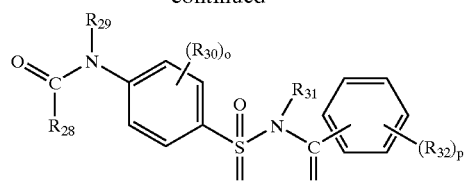

and of formula IIe

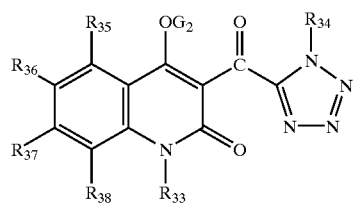

are suitable for protecting cultivated plants from the phytotoxic action of a particular class of specific, substituted 3-hydroxy-4-aryl-5-oxopyrazoline herbicides.

Accordingly, a selectively herbicidal composition is proposed according to the invention which, in addition to customary inert formulation assistants, for example carriers, solvents and wetting agents, comprises as active ingredient a mixture of a) a herbicidally effective amount of a herbicide of formula I

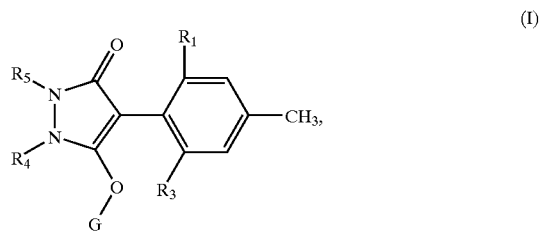

wherein $R_1$ and $R_3$ are, each independently of the other, ethyl, haloethyl, ethynyl, $C_1$- or $C_2$-alkoxy, $C_1$- or $C_2$-haloalkoxy, $C_1$- or $C_2$-alkylcarbonyl or $C_1$- or $C_2$-hydroxyalkyl;

$R_4$ and $R_5$ together are a group $Z_2$ —$CR_{14}(R_{15})$—$CR_{16}(R_{17})$—O—$CR_{18}(R_{19})$—$CR_{20}(R_{21})$— $(Z_2)$;

$R_{14}$, $R_{15}$, $R_{16}$, $R_{17}$, $R_{18}$, $R_{19}$, $R_{20}$ and $R_{21}$ are, each independently of the others, hydrogen, halogen, $C_1$–$C_4$alkyl or $C_1$–$C_4$haloalkyl, wherein an alkylene ring may be fused or spiro-bound to the carbon atoms of the group $Z_2$, which alkylene ring, together with the carbon atoms of the group $Z_2$, to which it is bonded, contains from 2 to 6 carbon atoms and may be interrupted by oxygen, or the alkylene ring bridges at least one ring atom of the group $Z_2$;

G is hydrogen, —$C(X_1)$—$R_{30}$, —$C(X_2)$—$X_3$—$R_{31}$, —$C(X_4)$—$NR_{32}(R_{33})$, —$S(O)_2$—$R_{34}$, —$P(X_5)R_{35}R_{36}$, —$CH_2$—$X_6$—$R_{37}$ or an alkali metal, alkaline earth metal, sulfonium or ammonium cation;

$X_1$, $X_2$, $X_3$, $X_4$, $X_5$ and $X_6$ are, each independently of the others, oxygen or sulfur;

$R_{30}$, $R_{31}$, $R_{32}$, $R_{33}$, $R_{34}$, $R_{35}$, $R_{36}$ and $R_{37}$ are, each independently of the others, hydrogen, $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_2$–$C_5$-alkenyl, $C_2$–$C_5$haloalkenyl, $C_3$–$C_8$cycloalkyl, $C_1$–$C_5$alkylamino-$C_1$–$C_5$alkyl, di($C_1$–$C_5$alkyl)amino-$C_1$–$C_5$alkyl, $C_3$–$C_7$cycloalkyl-$C_1$–$C_5$alkyl, $C_1$–$C_5$alkoxy-$C_1$–$C_5$alkyl, $C_3$–$C_5$alkenyloxy-$C_1$–$C_5$alkyl, $C_3$–$C_5$alkynyloxy-$C_1$–$C_5$alkyl, $C_1$–$C_5$alkylthio-$C_1$–$C_5$alkyl, $C_1$–$C_5$alkylsulfoxy-$C_1$–$C_5$alkyl, $C_1$–$C_5$-alkylsulfonyl-$C_1$–$C_5$alkyl, $C_2$–$C_8$alkylideneaminooxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$alkylaminocarbonyl-$C_1$–$C_5$alkyl, di($C_1$–$C_5$alkyl)aminocarbonyl-$C_1$–$C_5$alkyl, $C_1$–$C_5$alkylcarbonylamino-$C_1$–$C_5$alkyl, $C_1$–$C_5$alkylcarbonyl-($C_1$–$C_5$alkyl)-amino-$C_1$–$C_5$alkyl, tri($C_1$- or $C_2$-alkyl)silyl-$C_1$–$C_5$alkyl, phenyl, heteroaryl, phenyl-$C_1$–$C_5$alkyl, heteroaryl-$C_1$–$C_5$alkyl, phenoxy-$C_1$–$C_5$alkyl or heteroaryloxy-$C_1$–$C_5$alkyl, wherein the aforementioned aromatic rings may be substituted by halogen, nitro, cyano, amino, di($C_1$–$C_4$alkyl)-amino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl;

$R_{34}$, $R_{35}$ and $R_{36}$ are, in addition, $C_1$–$C_{10}$alkoxy, $C_1$–$C_{10}$haloalkoxy, $C_1$–$C_5$alkylamino, di($C_1$–$C_5$-alkyl)amino, benzyloxy or phenoxy, wherein the aromatic rings of the last two substituents may be substituted by halogen, nitro, cyano, amino, dimethylamino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl; and $R_{37}$ is, in addition, $C_1$–$C_{10}$alkylcarbonyl, or a salt or diastereoisomer of a compound of formula I, and b) an amount, which is effective for antagonism of the herbicide, of a safener of formula IIa

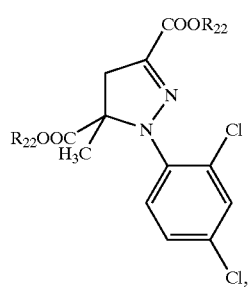

(IIa)

wherein $R_{22}$ is hydrogen, or an alkali metal, alkaline earth metal, sulfonium or ammonium cation, or ethyl, or of formula IIb

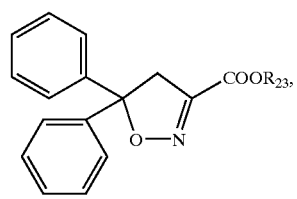

(IIb)

wherein $R_{23}$ is hydrogen, or an alkali metal, alkaline earth metal, sulfonium or ammonium cation, or ethyl, or of formula IIc

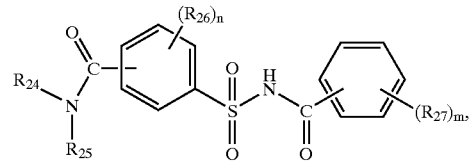

(IIc)

wherein $R_{24}$ and $R_{25}$ are, each independently of the other, hydrogen, $C_1$–$C_6$alkyl, $C_2$–$C_6$-alkenyl, $C_2$–$C_6$alkynyl or $C_3$–$C_6$cycloalkyl;

$R_{26}$ is hydrogen, halogen, $C_1$–$C_4$alkyl, $C_1$–$C_6$haloalkyl or $C_1$–$C_6$haloalkoxy; or the radicals $R_{26}$ are, each independently of the other(s), hydrogen, halogen, $C_1$–$C_4$alkyl, $C_1$–$C_6$haloalkyl or $C_1$–$C_6$haloalkoxy;

$R_{27}$ is hydrogen, halogen, $C_1$–$C_4$alkyl, $C_1$–$C_4$haloalkyl, $C_1$–$C_4$alkoxy, $C_1$–$C_4$haloalkoxy, $C_1$–$C_4$-alkylthio, $C_1$–$C_4$alkoxycarbonyl or nitro; or the radicals $R_{27}$ are, each independently of the other, hydrogen, halogen, $C_1$–$C_4$alkyl, $C_1$–$C_4$haloalkyl, $C_1$–$C_4$alkoxy, $C_1$–$C_4$haloalkoxy, $C_1$–$C_4$-alkylthio, $C_1$–$C_4$alkoxycarbonyl or nitro;

n is 0, 1, 2 or 3; and m is 1 or 2, or of formula IId

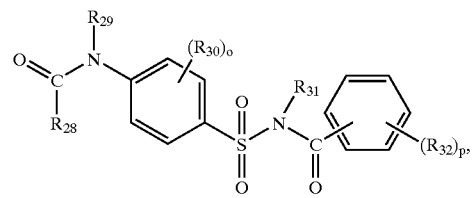

(IId)

wherein $R_{28}$ is hydrogen, $C_1$–$C_6$alkyl, $C_1$–$C_6$alkoxy, $C_1$–$C_6$alkylthio, $C_3$–$C_8$cycloalkyl, phenyl, phenyl-$C_1$–$C_6$alkyl or heteroaryl, wherein the afore-mentioned hydrocarbon radicals may be substituted by halogen, cyano, nitro, amino, hydroxy, carboxyl, formyl, carbonamide or by sulfonamide;

$R_{29}$ is hydrogen, $C_1$–$C_6$alkyl or $C_1$–$C_4$haloalkyl;

$R_{30}$ is hydrogen, halogen, $C_1$–$C_4$alkyl, $C_1$–$C_4$haloalkyl, $C_1$–$C_4$alkoxy, $C_1$–$C_4$alkylthio, $C_1$–$C_4$alkylsulfonyl, cyano, nitro, formyl or carboxyl; or the radicals $R_{30}$ are, each independently of the other hydrogen, halogen, $C_1$–$C_4$alkyl, $C_1$–$C_4$haloalkyl, $C_1$–$C_4$alkoxy, $C_1$–$C_4$alkylthio, $C_1$–$C_4$alkylsulfonyl, cyano, nitro, formyl or carboxyl;

$R_{31}$ is hydrogen, $C_1$–$C_6$alkyl or $C_1$–$C_4$haloalkyl;

$R_{32}$ is hydrogen, halogen, $C_1$–$C_4$alkyl, $C_1$–$C_4$haloalkyl, $C_1$–$C_4$alkoxy, $C_1$–$C_4$alkylthio, $C_1$–$C_4$alkylsulfonyl, cyano, nitro, formyl or carboxyl; or the radicals $R_{32}$ are, each independently of the other hydogen, halogen, $C_1$–$C_4$alkyl, $C_1$–$C_4$haloalkyl, $C_1$–$C_4$alkoxy, $C_1$–$C_4$alkylthio, $C_1$–$C_4$alkylsulfonyl, cyano, nitro, formyl or carboxyl; and o and p are, each independently of the other 0, 1 or 2, or of formula IIe

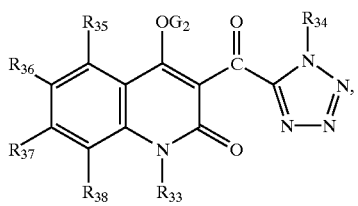

wherein
G$_2$ is hydrogen, formyl, C$_1$–C$_6$alkylcarbonyl, C$_2$–C$_6$alkenylcarbonyl, C$_2$–C$_6$alkynylcarbonyl, C$_1$–C$_6$alkoxycarbonyl, (C$_1$–C$_6$alkylthio)carbonyl, C$_3$–C$_8$cycloalkylcarbonyl, phenyl-C$_1$–C$_6$alkylcarbonyl, phenycarbonyl, C$_1$–C$_6$alkylsulfonyl, C$_2$–C$_6$alkenylsulfonyl or phenylsulfonyl, wherein the afore-mentioned hydrocarbon radicals may be substituted by halogen, cyano, nitro, amino, methoxy, ethoxy or by phenyl;

R$_{33}$ is hydrogen, C$_1$–C$_6$alkyl, C$_2$–C$_6$alkenyl, C$_2$–C$_6$alkynyl, C$_3$–C$_8$cycloalkyl, formyl, C$_1$–C$_6$alkylcarbonyl, C$_2$–C$_6$alkenylcarbonyl, C$_2$–C$_6$alkynylcarbonyl, C$_1$–C$_6$alkoxycarbonyl, (C$_1$–C$_6$alkylthio)carbonyl, C$_3$–C$_8$cycloalkylcarbonyl, C$_1$–C$_6$alkylsulfonyl, C$_2$–C$_6$alkenylsulfonyl or phenylsulfonyl, wherein the afore-mentioned hydrocarbon radicals may be substituted by halogen, cyano, nitro, amino, methoxy, ethoxy or by phenyl;

R$_{34}$ is hydrogen, C$_1$–C$_6$alkyl, C$_2$–C$_6$alkenyl, C$_2$–C$_6$alkynyl, C$_3$–C$_8$cycloalkyl, formyl, C$_1$–C$_6$alkylcarbonyl, C$_2$–C$_6$alkenylcarbonyl, C$_2$–C$_6$alkynylcarbonyl, C$_1$–C$_6$alkoxycarbonyl, (C$_1$–C$_6$alkylthio)carbonyl, C$_3$–C$_8$cycloalkylcarbonyl, C$_1$–C$_6$alkylsulfonyl, C$_2$–C$_6$alkenylsulfonyl or phenylsulfonyl, wherein the afore-mentioned hydrocarbon radicals may be substituted by halogen, cyano, nitro, amino, methoxy, ethoxy or by phenyl;

R$_{35}$, R$_{36}$, R$_{37}$ and R$_{38}$ are, each independently of the others, hydrogen, halogen, amino, C$_1$–C$_3$alkylamino, di(C$_1$–C$_3$alkyl)amino, hydroxy, cyano, nitro, formyl, carboxyl, C$_1$–C$_6$alkoxy, C$_1$–C$_6$haloalkoxy, C$_1$–C$_6$alkylcarbonyl, C$_1$–C$_6$alkoxycarbonyl, C$_1$–C$_6$alkyl, C$_1$–C$_6$haloalkyl, C$_2$–C$_6$-alkenyl or C$_2$–C$_6$alkynyl; or R$_{38}$ and R$_{33}$, together with the ring atoms to which they are bonded, form a five- or six-membered saturated or unsaturated ring that contains up to 2 identical or different hetero atoms selected from the group oxygen, sulfur and nitrogen and that may be interrupted by a —C(O)— radical.

Depending on the substituents R$_1$, R$_3$, R$_4$, R$_5$ and G, the compounds of formula I may be in the form of geometric and/or optical isomers and isomeric mixtures (atropisomers) and, when G is hydrogen, a metal ion equivalent, a sulfonium cation or an ammonium cation, in the form of tautomers and tautomeric mixtures.

The present invention also includes the salts that the compounds of formula I may form with acids. Suitable acids for the formation of acid addition salts are both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid.

The compounds of formula I wherein G is hydrogen can, because of their acidity, readily be converted, in the presence of bases (proton acceptors), into the corresponding salts (wherein G is, for example, a metal ion equivalent or an ammonium cation), as described, by example, in EP-A-0 508 126. Any conventional proton acceptor can be used as the base. The salts are, for example, alkali metal salts, e.g. sodium and potassium salts; alkaline earth metal salts, e.g. calcium and magnesium salts; ammonium salts, that is to say unsubstituted ammonium salts and mono- or poly-substituted ammonium salts, e.g. triethylammonium and methylammonium salts, or are salts with other organic bases or other cations, e.g. sulfonium cations. Sulfonium cations are, for example, tri(C$_1$–C$_4$alkyl)sulfonium cations, which can be obtained from the corresponding alkali metal salts, for example by salt conversion, for example using a cation exchanger.

Among the alkali metal and alkaline earth metal hydroxides used as salt formers, emphasis is to be given to, for example, the hydroxides of lithium, sodium, potassium, magnesium or calcium, but especially those of sodium and potassium. Suitable salt formers are described, for example, in WO 97/41112.

Examples of suitable amines for ammonium salt formation that come into consideration are ammonia as well as primary, secondary and tertiary C$_1$–C$_{18}$alkylamines, C$_1$–C$_4$hydroxyalkylamines and C$_2$–C$_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, isopropanolamine, N,N-diethanolamine, N-ethylpropanolamine, N-butyl-ethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thiomorpholine, piperidine, pyrrolidine, indoline, quinuclidine and azepine; primary aryl amines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

In the above definitions, halogen is to be understood as fluorine, chlorine, bromine or iodine, preferably fluorine, chlorine or bromine.

The alkyl groups occurring in the substituent definitions are, for example, methyl, ethyl, n-propyl, isopropyl, n-butyl, sec-butyl, isobutyl or tert-butyl, and the pentyl, hexyl, heptyl, octyl, nonyl and decyl isomers.

Haloalkyl groups preferably have a chain length of from 1 to 6 carbon atoms. Haloalkyl is, for example, fluoromethyl, difluoromethyl, difluorochloromethyl, trifluoromethyl, chloromethyl, dichloromethyl, dichlorofluoromethyl, trichloromethyl, 2,2,2-trifluoroethyl, 2-fluoroethyl, 2-chloroethyl, 2,2-difluoroethyl, 2,2-dichloroethyl, 2,2,2-trichloroethyl or pentafluoroethyl, preferably trichloromethyl, difluoromethyl, difluorochloromethyl, trifluoromethyl or dichlorofluoromethyl.

Alkoxy groups preferably have a chain length of from 1 to 6 carbon atoms. Alkoxy is, for example, methoxy, ethoxy, n-propoxy, isopropoxy, n-butoxy, isobutoxy, sec-butoxy, tert-butoxy, or a pentyloxy or hexyloxy isomer, preferably methoxy, ethoxy or n-propoxy.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy or 2,2,2-trichloroethoxy.

There may be mentioned as examples of alkenyl radicals vinyl, allyl, methallyl, 1-methylvinyl, but-2-en-1-yl, pentenyl and 2-hexenyl; preferably alkenyl radicals having a chain length of from 2 to 6 carbon atoms.

There may be mentioned as examples of alkynyl radicals ethynyl, propargyl, 1-methyl-propargyl, 3-butynyl, but-2-yn-1-yl, 2-methylbut-3-yn-2-yl, but-3-yn-2-yl, 1-pentynyl, pent-4-yn-1-yl and 2-hexynyl; preferably alkynyl radicals having a chain length of from 2 to 6 carbon atoms.

Suitable haloalkenyl radicals include alkenyl groups substituted one or more times by halogen, halogen being in particular bromine or iodine and especially fluorine or chlorine, for example 2- and 3-fluoropropenyl, 2- and 3-chloropropenyl, 2- and 3-bromopropenyl, 2,2-difluoro-1-methylvinyl, 2,3,3-trifluoropropenyl, 3,3,3-trifluoropropenyl, 2,3,3-trichloropropenyl, 4,4,4-trifluorobut-2-en-1-yl and 4,4,4-trichlorobut-2-en-1-yl. Preferred alkenyl radicals substituted once, twice or three times by halogen are those having a chain length of from 2 to 5 carbon atoms. The alkenyl groups may be substituted by halogen at saturated or unsaturated carbon atoms.

Alkenyloxy is, for example, allyloxy, methallyloxy or but-2-en-1-yloxy.

Alkynyloxy is, for example, propargyloxy or 1-methylpropargyloxy.

Alkoxyalkyl groups have preferably from 2 to 10 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Suitable cycloalkyl substituents contain from 3 to 8 carbon atoms and are, for example, cyclopropyl, cyclobutyl, cyclopentyl, cyclohexyl, cycloheptyl or cyclooctyl.

Alkylcarbonyl is especially acetyl or propionyl.

Alkoxycarbonyl is, for example, methoxycarbonyl, ethoxycarbonyl, n-propoxycarbonyl, isopropoxycarbonyl or a butoxycarbonyl, pentyloxycarbonyl or hexyloxycarbonyl isomer, preferably methoxycarbonyl or ethoxycarbonyl.

Phenyl per se or as part of a substituent, for example phenoxyalkyl or benzyloxy, may be in substituted form, in which case the substituents may, as desired, be in the ortho-, meta- and/or para-position. Preferred positions for the substituents are the ortho- and para-position to the ring attachment point. Phenyl substituents are, for example, halogen, $C_1$- or $C_2$-haloalkyl, hydroxy, $C_1$- or $C_2$-alkoxy, $C_1$–$C_5$alkoxycarbonyl, $C_1$- or $C_2$alkylthio, formyl, acetyl, propionyl, carboxyl, nitro, cyano, amino or dimethylamino.

Alkylthio groups preferably have a chain length of from 1 to 5 carbon atoms. Alkylthio is, for example, methylthio, ethylthio, propylthio, butylthio, pentylthio or hexylthio, or a branched isomer thereof, but is preferably methylthio or ethylthio.

Alkylsulfoxy is, for example, methylsulfoxy, ethylsulfoxy, n-propylsulfoxy, isopropylsulfoxy, n-butylsulfoxy, isobutylsulfoxy, sec-butylsulfoxy or tert-butylsulfoxy, preferably methylsulfoxy or ethylsulfoxy.

Alkylsulfonyl is, for example, methylsulfonyl, ethylsulfonyl, n-propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamine or a butyl- or pentyl-amine isomer.

Dialkylamino is, for example, dimethylamino, methylethylamino, diethylamino, n-propyl-methylamino, dibutylamino or diisopropylamino.

Alkylthioalkyl is, for example, methylthiomethyl, methylthioethyl, ethylthiomethyl, ethylthioethyl, n-propylthiomethyl, n-propylthioethyl, isopropylthiomethyl or isopropylthioethyl.

Hydroxyalkyl is, for example, hydroxymethyl, 2-hydroxyethyl or 3-hydroxypropyl.

Cyanoalkyl is, for example, cyanomethyl, cyanoethyl, cyanoeth-1-yl or cyanopropyl.

Aminoalkyl is, for example, aminomethyl, aminoethyl, aminoeth-1-yl or aminopropyl.

Nitroalkyl is, for example, nitromethyl, 2-nitroethyl or 3-nitropropyl.

Alkylideneaminooxy-alkyl radicals are oxime ether substituents, for example having the following structure $$H_3C-\overset{H}{\underset{N}{C}}=N-O-alkyl---.$$

Carbonamide and sulfonamide radicals, for example in the definition of $R_{28}$, have the structures —C(O)NH$_2$ and —S(O)$_2$NH$_2$, respectively.

Heteroaryl radicals per se or as part of a substituent, for example heteroaryloxy-alkyl, are usually 5- or 6-membered aromatic heterocycles that contain preferably from 1 to 3 hetero atoms, such as N, S and/or O. Examples of suitable heteroaryl radicals are pyridyl, pyrimidyl, thienyl, triazinyl, thiazolyl, triazolyl, thiadiazolyl, imidazolyl, oxazolyl, isoxazolyl, pyrazinyl, furyl, pyrazolyl, benzoxazolyl, benzothiazolyl, quinoxalyl, indolyl and quinolyl. Those hetero-aromatic radicals may, in addition, be substituted, for example by halogen, $C_1$- or $C_2$-halo-alkyl, hydroxy, $C_1$- or $C_2$-alkoxy, $C_1$- or $C_2$alkylthio, formyl, acetyl, propionyl, carboxyl, $C_1$–$C_5$-alkoxycarbonyl, amino, dimethylamino, nitro or by cyano.

Meanings corresponding to those given hereinbefore can also be ascribed to the substituents in composite definitions, such as, for example alkylamino-alkyl, dialkylamino-alkyl, cycloalkyl-alkyl, alkenyloxy-alkyl, alkynyloxy-alkyl, alkylsulfoxy-alkyl, alkylsulfonyl-alkyl, alkylcarbonyl-alkyl, alkoxycarbonyl-alkyl, alkylaminocarbonyl-alkyl, dialkylaminocarbonyl-alkyl, alkylcarbonylamino-alkyl, alkylcarbonyl(alkyl)-amino-alkyl, phenyl-alkyl and heteroaryl-alkyl.

Compounds of formula I wherein an alkylene ring may be fused or spiro-bound to the group $Z_2$, which alkylene ring, together with the carbon atoms of the group $Z_2$, contains from 2 to 6 carbon atoms, have, for example, the following structure (spiro-linked) or -continued

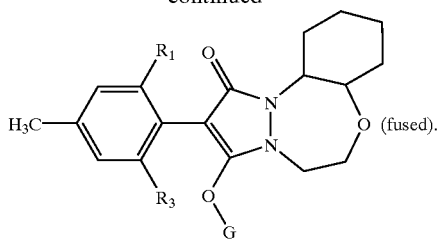 (fused).

Compounds of formula I wherein in the group $Z_2$ an alkylene ring bridges at least one ring atom of the group $Z_2$ have, for example, the following structure

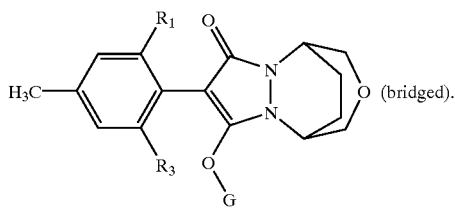 (bridged).

In the definitions for cyanoalkyl, alkylcarbonyl, alkylcarbonylamino and alkoxycarbonyl, the carbon atom of the cyano or carbonyl is not included in the lower and upper limits given for the number of carbons in each particular case.

The compounds of formula I, except for those derivatives wherein G is $-CH_2-X_6-R_{27}$, are known from WO 99/47525 and can be prepared analogously to the methods described therein and in EP-A-0 508 126.

The compounds of formula IIa are known from DE-A-3 939 503, those of formula IIb from DE-A-4 331 448, those of formula IIc from WO 99/16744, those of formula IId from WO 00/30447 and those of formula IIe from WO 00/00020.

The compounds of formula Ia

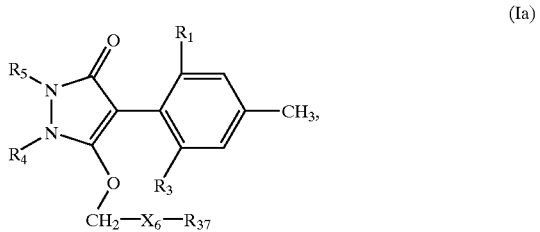

(Ia)

wherein $R_1$, $R_3$, $R_4$, $R_5$, $R_{37}$ and $X_6$ are as defined for formula I, are new and are therefore also included in the present invention.

The compounds of formula Ia can be prepared using processes known per se, for example by converting a compound of formula Ib

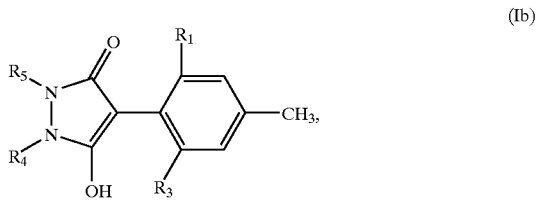

(Ib)

in an inert solvent, for example an aromatic hydrocarbon, e.g. benzene, toluene or a xylene; a chlorinated hydrocarbon, e.g. dichloromethane or chlorobenzene; a ketone, e.g. acetone or 2-butanone; a nitrile, e.g. acetonitrile or propionitrile; an ether, e.g. diethyl ether, tert-butyl-methyl ether or di-n-propyl ether; an ester, e.g. ethyl acetate; an amide, e.g. N,N-dimethyl-formamide or N-methylpyrrolidone (NMP); a sulfoxide, e.g. dimethyl sulfoxide (DMSO) or a sulfone, e.g. sulfolane, in the presence of a base, for example an alkylamine, e.g. triethylamine or diisopropylethylamine; an alicyclic or aromatic amine, e.g. 1,4-diazabicyclo[2.2.2]-octane (DABCO) or 1,8-diazabicyclo[5.4.0]undec-7-ene (DBU) or pyridine; a carbonate, e.g. sodium or potassium carbonate, or sodium or potassium bicarbonate, into the corresponding salt of formula Ic

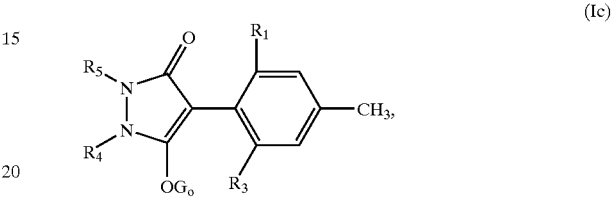

(Ic)

wherein the radicals $R_1$, $R_3$, $R_4$ and $R_5$ in the compounds of formulae Ib and Ic are as defined for formula I and $G_0$ is an alkali metal, alkaline earth metal, ammonium or sulfonium cation, depending on the base used, and then reacting the compound of formula Ic with a compound of formula III $$R_{37}-X_6-CH_2-Y \quad (III),$$

wherein $R_{37}$ and $X_6$ are as defined for formula I and Y is a leaving group, for example halogen, e.g. chlorine, bromine or iodine, at temperatures of from −20° C. to reflux temperature, preferably at from 0° C. to the reflux temperature of the solvent used.

The Example that follows illustrates the preparation of compounds of formula Ia.

EXAMPLE P1

Preparation of

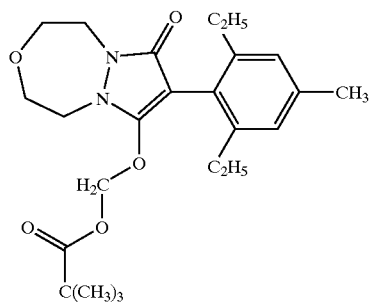

0.753 g of pivalic acid chloromethyl ester is added to 0.75 g of sodium iodide dissolved in 20 ml of acetone, and the reaction mixture is stirred overnight at 25° C. The reaction mixture is cooled to 5° C.; 1.58 g of 8-(2,6-diethyl-4-methylphenyl)tetrahydropyrazolo[1,2-d][1,4,5]-oxadiazepine-7,9-dione and 0.69 g of potassium carbonate are added and the reaction mixture is stirred first for one hour at 5° C. and then for 24 hours at 25° C. The resulting reaction mixture is filtered and the filtrate is concentrated by evaporation under reduced pressure. The residue is dissolved in 100 ml of ethyla acetate, washed with water until neutral, dried over sodium sulfate and concentrated by evaporation.

The preferred compounds of formula Ia listed in Table 1 below are prepared in an analogous manner.

TABLE 1

Compounds of formula Ia

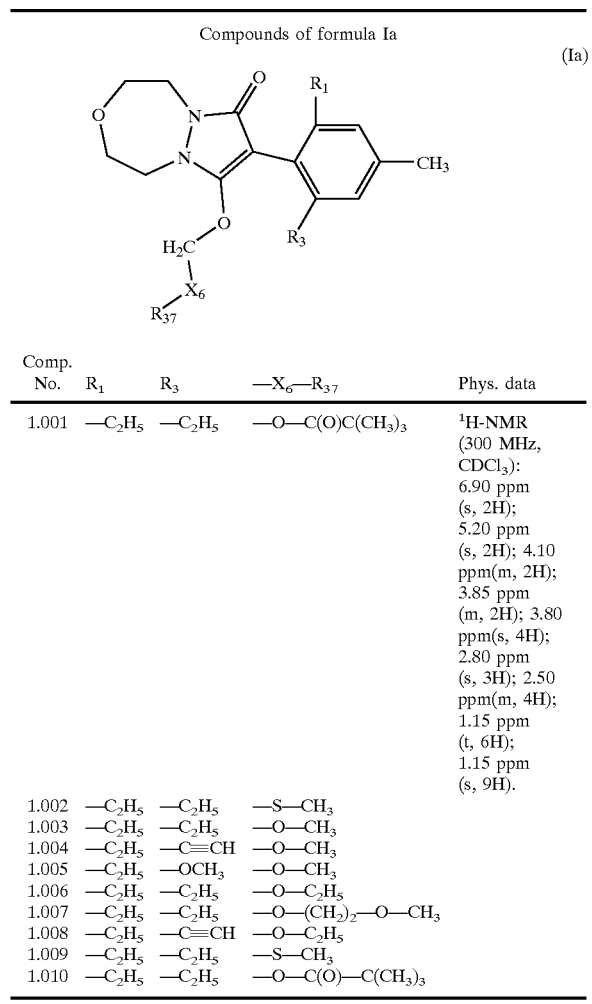

(Ia)

| Comp. No. | $R_1$ | $R_3$ | —$X_6$—$R_{37}$ | Phys. data |
|---|---|---|---|---|
| 1.001 | —$C_2H_5$ | —$C_2H_5$ | —O—C(O)C($CH_3$)$_3$ | $^1$H-NMR (300 MHz, CDCl$_3$): 6.90 ppm (s, 2H); 5.20 ppm (s, 2H); 4.10 ppm(m, 2H); 3.85 ppm (m, 2H); 3.80 ppm(s, 4H); 2.80 ppm (s, 3H); 2.50 ppm(m, 4H); 1.15 ppm (t, 6H); 1.15 ppm (s, 9H). |
| 1.002 | —$C_2H_5$ | —$C_2H_5$ | —S—$CH_3$ | |
| 1.003 | —$C_2H_5$ | —$C_2H_5$ | —O—$CH_3$ | |
| 1.004 | —$C_2H_5$ | —C≡CH | —O—$CH_3$ | |
| 1.005 | —$C_2H_5$ | —$OCH_3$ | —O—$CH_3$ | |
| 1.006 | —$C_2H_5$ | —$C_2H_5$ | —O—$C_2H_5$ | |
| 1.007 | —$C_2H_5$ | —$C_2H_5$ | —O—($CH_2$)$_2$—O—$CH_3$ | |
| 1.008 | —$C_2H_5$ | —C≡CH | —O—$C_2H_5$ | |
| 1.009 | —$C_2H_5$ | —$C_2H_5$ | —S—$CH_3$ | |
| 1.010 | —$C_2H_5$ | —$C_2H_5$ | —O—C(O)—C($CH_3$)$_3$ | |

Herbicides of formula I that are preferred for the composition according to the invention are those wherein $R_1$ and $R_3$ are, each independently of the other, ethyl, haloethyl, ethynyl, $C_1$- or $C_2$-alkoxy or $C_1$- or $C_2$-haloalkoxy.

In a further group of preferred compounds of formula I, $R_4$ and $R_5$ together form a group of $Z_2$ —$CR_{14}(R_{15})$—$CR_{16}(R_{17})$—O—$CR_{18}(R_{19})$—$CR_{20}(R_{21})$— ($Z_2$), wherein $R_{14}$, $R_{15}$, $R_{16}$, $R_{17}$, $R_{18}$, $R_{19}$, $R_{20}$ and $R_{21}$ are hydrogen.

Preference is given also to those compounds of formula I wherein G is hydrogen, —C($X_1$)—$R_{30}$, —C($X_2$)—$X_3$—$R_{31}$, —C($X_4$)—$NR_{32}(R_{33})$, —S(O)$_2$—$R_{34}$, —P($X_5$)$R_{35}R_{36}$, —$CH_2$—$X_6$—$R_{37}$ or an alkali metal, alkaline earth metal, sulfonium or ammonium cation; $X_1$, $X_2$, $X_3$, $X_4$, $X_5$ and $X_6$ are, each independently of the others, oxygen or sulfur; $R_{30}$, $R_{31}$, $R_{32}$, $R_{33}$, $R_{34}$, $R_{35}$, $R_{36}$ and $R_{37}$ are, each independently of the others, hydrogen, $C_1$–$C_8$alkyl, $C_1$–$C_8$haloalkyl, $C_1$–$C_8$cyanoalkyl, $C_1$–$C_8$nitroalkyl, $C_1$–$C_8$aminoalkyl, $C_2$–$C_5$-alkenyl, $C_2$–$C_5$haloalkenyl, $C_3$–$C_8$cycloalkyl, $C_1$–$C_5$alkylamino-$C_1$–$C_2$alkyl, di($C_1$–$C_5$alkyl)amino-$C_1$–$C_2$alkyl, $C_3$–$C_7$cycloalkyl-$C_1$–$C_2$alkyl, $C_1$–$C_4$alkoxy-$C_1$–$C_4$alkyl, $C_2$–$C_4$alkenyloxy-$C_1$–$C_4$alkyl, $C_3$–$C_4$alkynyloxy-$C_1$–$C_4$alkyl, $C_1$–$C_4$alkylthio-$C_1$–$C_4$alkyl, $C_1$–$C_2$alkylsulfoxy-$C_1$–$C_2$alkyl, $C_1$–$C_2$-alkylsulfonyl-$C_1$–$C_2$alkyl, $C_2$–$C_8$alkylideneaminooxy-$C_1$–$C_2$alkyl, $C_1$–$C_5$alkylcarbonyl-$C_1$–$C_2$alkyl, $C_1$–$C_5$alkoxycarbonyl-$C_1$–$C_2$alkyl, $C_1$–$C_5$alkylaminocarbonyl-$C_1$–$C_2$alkyl, di($C_1$–$C_4$alkyl)aminocarbonyl-$C_1$–$C_2$alkyl, $C_1$–$C_5$alkylcarbonylamino-$C_1$–$C_2$alkyl, $C_1$–$C_2$alkylcarbonyl-($C_1$–$C_3$alkyl)-amino-$C_1$–$C_2$alkyl, tri($C_1$- or $C_2$-alkyl)silyl-$C_1$–$C_3$-alkyl, phenyl, heteroaryl, phenyl-$C_1$–$C_2$alkyl, heteroaryl-$C_1$–$C_2$alkyl, phenoxy-$C_1$–$C_2$alkyl or heteroaryloxy-$C_1$–$C_2$alkyl; $R_{34}$, $R_{35}$ and $R_{36}$ are, in addition, $C_1$–$C_6$alkoxy, $C_1$–$C_6$haloalkoxy, $C_1$–$C_3$alkylamino, di($C_1$–$C_3$alkyl)amino, benzyloxy or phenoxy, wherein the aromatic rings of the last two substituents may be substituted by halogen, nitro, cyano, amino, dimethylamino, hydroxy, methoxy, ethoxy, methylthio, ethylthio, formyl, acetyl, propionyl, carboxyl, $C_1$–$C_5$-alkoxycarbonyl or by $C_1$- or $C_2$-haloalkyl; and $R_{37}$ is, in addition, $C_1$–$C_8$alkylcarbonyl.

Among those, special preference is given to those compounds wherein G is hydrogen, —C($X_1$)—$R_{30}$, —C($X_2$)—$X_3$—$R_{31}$, —C($X_4$)—$NR_{32}(R_{33})$, —S(O)$_2$—$R_{34}$, —P($X_5$)$R_{35}R_{36}$, —$CH_2$—$X_6$—$R_{37}$ or an alkali metal, alkaline earth metal, sulfonium or ammonium cation; $X_1$, $X_2$, $X_3$, $X_4$, $X_5$ and $X_6$ are, each independently of the others, oxygen or sulfur; $R_{30}$, $R_{31}$, $R_{32}$, $R_{33}$, $R_{34}$, $R_{35}$, $R_{36}$ and $R_{37}$ are, each independently of the others, hydrogen, $C_1$–$C_8$alkyl, $C_1$–$C_8$haloalkyl, $C_1$–$C_8$alkenyl, $C_2$–$C_5$haloalkenyl, $C_3$–$C_8$cycloalkyl, $C_3$–$C_7$cycloalkyl-$C_1$–$C_2$alkyl, $C_1$–$C_4$alkoxy-$C_1$–$C_4$alkyl, phenyl, heteroaryl, phenyl-$C_1$–$C_2$alkyl, heteroaryl-$C_1$–$C_2$alkyl, phenoxy-$C_1$–$C_2$alkyl or heteroaryloxy-$C_1$–$C_2$alkyl; $R_{34}$, $R_{35}$ and $R_{36}$ are, in addition, $C_1$–$C_6$alkoxy, $C_1$–$C_3$alkylamino or di($C_1$–$C_3$alkyl)amino; and $R_{37}$ is, in addition, $C_1$–$C_8$alkylcarbonyl.

Preference is also given to those compounds of formula I wherein G is —$CH_2$—$X_6$—$R_{37}$ and $X_6$ and $R_{37}$ are as defined for formula I.

Preference is likewise given to compounds of formula I wherein $R_1$ or $R_3$ is, or $R_1$ and $R_3$ are, each independently of the other $C_1$- or $C_2$-haloalkoxy or $C_1$- or $C_2$-hydroxyalkyl.

Preference is also given to compounds of formula I wherein G is —C($X_1$)—$R_{30}$, —C($X_2$)—$X_3$—$R_{31}$, —C($X_4$)—$NR_{32}(R_{33})$, —S(O)$_2$—$R_{34}$ or —P($X_5$)$R_{35}R_{36}$; $X_1$, $X_2$, $X_3$, $X_4$ and $X_5$ are, each independently of the others, oxygen or sulfur; $R_{30}$, $R_{31}$, $R_{32}$, $R_{33}$, $R_{34}$, $R_{35}$ and $R_{36}$ are, each independently of the others, $C_1$–$C_{10}$cyanoalkyl, $C_1$–$C_{10}$nitroalkyl, $C_1$–$C_{10}$aminoalkyl, $C_1$–$C_5$alkylamino-$C_1$–$C_5$alkyl, di($C_1$–$C_5$alkyl)amino-$C_1$–$C_5$-alkyl, $C_3$–$C_7$cycloalkyl-$C_1$–$C_5$alkyl, $C_3$–$C_5$alkenyloxy-$C_1$–$C_5$alkyl, $C_3$–$C_5$alkynyloxy-$C_1$–$C_5$alkyl, $C_1$–$C_5$alkylthio-$C_1$–$C_5$alkyl, $C_1$–$C_5$alkylsulfoxy-$C_1$–$C_5$alkyl, $C_1$–$C_5$alkylsulfonyl-$C_1$–$C_5$alkyl, $C_2$–$C_8$-alkylideneaminooxy-$C_1$–$C_5$alkyl, $C_1$–$C_5$alkylcarbonyl-$C_1$–$C_5$alkyl, $C_1$–$C_5$alkoxycarbonyl-$C_1$–$C_5$-alkyl, $C_1$–$C_5$alkylaminocarbonyl-$C_1$–$C_5$alkyl, di($C_1$–$C_5$alkyl)aminocarbonyl-$C_1$–$C_5$alkyl, $C_1$–$C_5$-alkylcarbonylamino-$C_1$–$C_5$alkyl, $C_1$–$C_5$alkylcarbonyl-($C_1$–$C_5$alkyl)-amino-$C_1$–$C_5$alkyl, tri($C_1$- or $C_2$-alkyl)silyl-$C_1$–$C_5$alkyl, phenyl-$C_1$–$C_5$alkyl, heteroaryl-$C_1$–$C_5$alkyl, phenoxy-$C_1$–$C_5$alkyl or heteroaryloxy-$C_1$–$C_5$alkyl, wherein the afore-mentioned aromatic rings may be substituted by halogen, nitro, cyano, amino, di($C_1$–$C_4$alkyl)amino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl; and $R_{34}$, $R_{35}$ and $R_{36}$ are, in addition, $C_1$–$C_{10}$alkoxy, $C_1$–$C_{10}$haloalkoxy, $C_1$–$C_5$alkylamino, di($C_1$–$C_5$-alkyl)amino, benzyloxy or phenoxy, wherein the aromatic rings of the last two substituents may be substituted by halogen, nitro, cyano, amino, dimethylamino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl.

Preferred selectively herbicidal compositions are those which comprise as active ingredient a mixture of a) a herbicidally effective amount of a herbicide of formula I, wherein $R_1$, $R_3$, $R_4$, $R_5$ and G are as defined for formula I, and b) an amount, which is effective for antagonism of the herbicide, of a safener of formula IIa, wherein $R_{22}$ is as defined for formula IIa, or of formula IIb, wherein $R_{23}$ is as defined for formula IIb, or of formula IIc, wherein $R_{24}$ and $R_{25}$ are, each independently of the other, hydrogen, $C_1$–$C_6$alkyl, $C_2$–$C_6$alkenyl, $C_2$–$C_6$-alkynyl or $C_3$–$C_6$cycloalkyl;

$R_{26}$ is halogen, $C_1$–$C_4$alkyl or $C_1$–$C_4$haloalkyl;

$R_{27}$ is halogen, $C_1$–$C_4$alkyl, $C_1$–$C_4$haloalkyl, $C_1$–$C_4$alkoxy, $C_1$–$C_4$alkylthio, $C_1$–$C_4$alkoxycarbonyl or nitro;

n is 0, 1, 2 or 3; and m is 1 or 2.

Safeners of formula IIa preferred for the composition according to the invention are those wherein $R_{22}$ is hydrogen or an alkali metal, alkaline earth metal, sulfonium or ammonium cation.

Safeners of formulae IIa and IIb preferred for the composition according to the invention are those wherein $R_{22}$ and $R_{23}$ are ethyl and are referred to hereinafter as safeners of formulae IIa$_1$ and IIb$_1$ (Biological Examples). They are known under the names mefenpyr-ethyl (compound no. IIa$_1$) and isoxadifen-ethyl (compound no. IIb$_1$) (ISO proposed names).

Safeners of formula IId preferred for the composition according to the invention are those wherein $R_{28}$ is hydrogen, $C_1$–$C_6$alkyl, $C_3$–$C_8$cycloalkyl or phenyl, wherein the afore-mentioned hydrocarbon radicals may be substituted by halogen, cyano, nitro, amino, hydroxy, carboxyl, formyl, carbonamide or by sulfonamide; $R_{29}$ is hydrogen; $R_{30}$ is hydrogen, halogen, $C_1$–$C_4$-alkyl, alkyl, $C_1$–$C_4$haloalkyl, $C_1$–$C_4$alkoxy, $C_1$–$C_4$alkylthio, cyano, nitro or formyl; or the radicals $R_{30}$ are, each independently of the other, hydrogen, halogen, $C_1$–$C_4$alkyl, $C_1$–$C_4$haloalkyl, $C_1$–$C_4$-alkoxy, $C_1$–$C_4$alkylthio, cyano, nitro or formyl; $R_{31}$ is hydrogen; $R_{32}$ is hydrogen, halogen, $C_1$–$C_4$alkyl, $C_1$–$C_4$haloalkyl, $C_1$–$C_4$alkoxy, $C_1$–$C_4$alkylthio, cyano, nitro or formyl; or the radicals $R_{32}$ are, each independently of the other, hydrogen, halogen, $C_1$–$C_4$alkyl, $C_1$–$C_4$haloalkyl, $C_1$–$C_4$alkoxy, $C_1$–$C_4$alkylthio, cyano, nitro or formyl; and o and p are, each independently of the other, 0, 1 or 2.

Safeners of formula IId that are especially preferred for the composition according to the invention are:

2-methoxy-N-[4-(2-methoxybenzoylsulfamoyl)phenyl]acetamide;

N-[4-(2-methoxybenzoylsulfamoyl)phenyl]cyclopropanecarboxamide;

N-[4-(2-methoxybenzoylsulfamoyl)phenyl]cyclobutanecarboxamide;

N-[4-(2-chlorobenzoylsulfamoyl)phenyl]cyclopropanecarboxamide;

N-[4-(2-chlorobenzoylsulfamoyl)phenyl]acetamide;

N-[4-(2-trifluoromethoxybenzoylsulfamoyl)phenyl]acetamide;

N-[4-(2-trifluoromethylbenzoylsulfamoyl)phenyl]cyclopropanecarboxamide;

N-[4-(2-trifluoromethoxybenzoylsulfamoyl)phenyl]cyclopropanecarboxamide;

N-[4-(2-trifluoromethoxybenzoylsulfamoyl)phenyl]cyclobutanecarboxamide; and

N-[4-(2-trifluoromethylbenzoylsulfamoyl)phenyl]acetamide.

Safeners of formula IIe preferred for the composition according to the invention are those wherein $G_2$ is hydrogen, formyl, $C_1$–$C_6$alkylcarbonyl, $C_2$–$C_6$alkenylcarbonyl, $C_2$–$C_6$alkynylcarbonyl, $C_1$–$C_6$alkoxycarbonyl, ($C_1$–$C_6$alkylthio)carbonyl, $C_3$–$C_8$cycloalkylcarbonyl, phenyl-$C_1$–$C_6$alkylcarbonyl or phenylcarbonyl, wherein the afore-mentioned hydrocarbon radicals may be substituted by halogen, cyano, nitro, amino, methoxy, ethoxy or by phenyl; $R_{33}$ is hydrogen, $C_1$–$C_6$alkyl, $C_2$–$C_6$alkenyl, $C_2$–$C_6$alkynyl, formyl, $C_1$–$C_6$alkylcarbonyl or $C_1$–$C_6$alkoxycarbonyl, wherein the afore-mentioned hydrocarbon radicals may be substituted by halogen, cyano, nitro, amino, methoxy, ethoxy or by phenyl; $R_{34}$ is hydrogen, $C_1$–$C_6$alkyl, $C_2$–$C_6$alkenyl, $C_2$–$C_6$alkynyl, formyl, $C_1$–$C_6$alkylcarbonyl or $C_1$–$C_6$-alkoxycarbonyl, wherein the afore-mentioned hydrocarbon radicals may be substituted by halogen, cyano, nitro, amino, methoxy, ethoxy or by phenyl; $R_{35}$, $R_{36}$, $R_{37}$ and $R_{38}$ are, each independently of the others, hydrogen, halogen, cyano, nitro, formyl, carboxyl, $C_1$–$C_6$alkoxy, $C_1$–$C_6$haloalkoxy, $C_1$–$C_6$alkylcarbonyl, $C_1$–$C_6$alkoxycarbonyl, $C_1$–$C_6$alkyl or $C_1$–$C_6$haloalkyl; or $R_{38}$ and $R_{33}$, together with the ring atoms to which they are bonded, form a five- or six-membered saturated or unsaturated ring that contains up to 2 identical or different hetero atoms selected from the group oxygen, sulfur and nitrogen and that may be interrupted by a —C(O)— radical.

Among those, special preference is given to those compounds wherein $G_2$ is hydrogen, formyl, $C_1$–$C_6$alkylcarbonyl, $C_2$–$C_6$alkenylcarbonyl, $C_2$–$C_6$alkynylcarbonyl, $C_1$–$C_6$alkoxycarbonyl, ($C_1$–$C_6$alkylthio)carbonyl, $C_3$–$C_8$cycloalkylcarbonyl or phenylcarbonyl; $R_{33}$ is hydrogen, $C_1$–$C_6$alkyl, $C_2$–$C_6$alkenyl, $C_2$–$C_6$alkynyl, formyl, $C_1$–$C_6$alkylcarbonyl or $C_1$–$C_6$alkoxycarbonyl; $R_{34}$ is hydrogen, $C_1$–$C_6$alkyl, $C_2$–$C_6$alkenyl, $C_2$–$C_6$alkynyl, formyl, $C_1$–$C_6$alkylcarbonyl or $C_1$–$C_6$-alkoxycarbonyl; $R_{35}$, $R_{36}$, $R_{37}$ and $R_{38}$ are, each independently of the others, hydrogen, halogen, cyano, nitro, formyl, $C_1$–$C_6$alkyl, $C_1$–$C_6$haloalkyl, $C_1$–$C_6$alkoxy or $C_1$–$C_6$haloalkoxy; or $R_{38}$ and $R_{33}$, together with the ring atoms to which they are bonded, form a five- or six-membered saturated or unsaturated ring that contains up to 2 identical or different hetero atoms selected from the group oxygen, sulfur and nitrogen and that may be interrupted by a —C(O)— radical.

Safeners of formula IIe that are especially preferred for the composition according to the invention are:

4-hydroxy-1-methyl-3-(1H-tetrazole-5-carbonyl)-1H-quinolin-2-one;

1-ethyl-4-hydroxy-3-(1H-tetrazole-5-carbonyl)-1H-quinolin-2-one;

6-hydroxy-5-(1H-tetrazole-5-carbonyl)-1,2-dihydropyrrolo[3,2,1-H]quinolin-4-one;

3-(1-acetyl-1H-tetrazole-5-carbonyl)-4-hydroxy-1-methyl-1H-quinolin-2-one;

6-chloro-4-hydroxy-1-methyl-3-(1H-tetrazole-5-carbonyl)-1H-quinolin-2-one;

6-fluoro-4-hydroxy-1-methyl-3-(1H-tetrazole-5-carbonyl)-1H-quinolin-2-one;

4-hydroxy-1,6-dimethyl-3-(1H-tetrazole-5-carbonyl)-1H-quinolin-2-one;

4-hydroxy-6-methoxy-1-methyl-3-(1H-tetrazole-5-carbonyl)-1H-quinolin-2-one;

1-methyl-2-oxo-3-(1H-tetrazole-5-carbonyl)-1,2-dihydroquinolin-4-yl acetate; and 1-methyl-2-oxo-3-(1H-tetrazole-5-carbonyl)-1,2-dihydroquinolin-4-yl 2,2-dimethyl propionate.

The invention relates also to a method for the selective control of weeds in crops of useful plants, which method comprises treating the useful plants, their seeds or seedlings or the crop area thereof with, simultaneously or separately, a) a herbicidally effective amount of a herbicide of formula I, b) an amount, which is effective for antagonism of the herbicide, of a safener of formula II and, optionally, c) an additive comprising an oil of vegetable origin or an alkylated derivative thereof, or a mineral oil or a mixture thereof.

Cultivated plants that may be protected against the harmful effect of the above-mentioned herbicides by means of the safeners of formula II are especially cereals, maize and sorghum. Crops are to be understood as including those that have been made tolerant to herbicides or classes of herbicides by means of conventional breeding or genetic engineering methods, for example IMI Maize, Poast Protected Maize (Sethoxydim tolerance), Liberty Link Maize, B.t./Liberty Link Maize, IMI/Liberty Link Maize, IMI/Liberty Link/B.t. Maize, Roundup Ready Maize and Roundup Ready/B.t. Maize. The weeds to be controlled may be both monocots and dicots, for example *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica.*

Crop areas are areas of land on which the cultivated plants are already growing or in which the seeds of those cultivated plants have been sown, and also areas of land on which it is intended to grow those cultivated plants.

A safener of formula II may, depending on the intended purpose, be used to pre-treat the seed material of the cultivated plant (dressing the seed or the seedlings) or may be incorporated into the soil before or after sowing. It may, however, also be applied, alone or together with the herbicide and, optionally, the oil additive, after the emergence of the plants. The treatment of the plants or seed with the safener can therefore, in principle, be effected independently of the time at which the herbicide is applied. The treatment of the plant can, however, also be carried out by applying the herbicide and the safener simultaneously (for example in the form of a tank mixture). The rate of application of the safener in relation to the herbicide depends largely on the method of application. In the case of field treatment, which is effected either using a tank mixture with a combination of the safener and the herbicide or by the separate application of the safener and the herbicide, the ratio of herbicide to safener is generally from 1:100 to 100:1, preferably from 1:10 to 10:1, and especially from 1:5 to 5:1.

In the case of field treatment, from 0.001 to 5.0 kg safener/ha, preferably from 0.001 to 0.5 kg safener/ha, are generally applied. The rate of application of herbicide is generally from 0.001 to 2 kg/ha, but preferably from 0.005 to 0.5 kg/ha.

In addition to the conventional formulation adjuvants, oil additives c) may be introduced as additives into the spray tank (as a tank mixture), besides surfactants and salts. In the composition according to the invention, the amounts of oil additive employed are generally from 0.01 to 2% based on the spray mixture. The oil additive can, for example, be added to the spray tank in the desired concentration after the spray mixture has been prepared. Suitable oil additives include emulsifiable oil concentrates of mineral oils or, especially, of vegetable oils. Preferred vegetable oil concentrates comprise, for example, the following 4 components (A) from 20 to 90% by weight of alkyl esters of higher fatty acids ($C_4$–$C_{22}$), (B) from 4 to 40% by weight of anionic or non-ionic surfactants, (C) from 2 to 20% by weight of higher fatty acids ($C_{10}$–$C_{20}$), and (D) up to 140% by weight, based on the total amount of components (A) to (C), of hydrocarbons.

Especially preferred oil additives c) comprise alkyl esters of higher fatty acids ($C_8$–$C_{22}$), especially the $C_1$–$C_4$alkyl ester derivatives of $C_{12}$–$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9). The application and action of the oil additives can be improved by combining them with surface-active substances, for example anionic surfactants (B). Examples of suitable anionic surfactants are listed in WO 97/34485 on pages 7 and 8. Preferred surface-active substances are anionic surfactants of the dodecylbenzylsulfonate type, especially the calcium salts thereof. The concentration of the surface-active substances based on the total additive is generally from 1 to 30% by weight.

Preferred higher fatty acids (C) have from 12 to 18 carbon atoms. The addition of an organic solvent (D) to the oil additive/surfactant/fatty acid mixture can, furthermore, bring about a further increase in action. Suitable solvents (D) are, for example, aromatic solvents, e.g. Solvesso® (ESSO) or Aromatic Solvent® (Exxon Corporation) types. The concentration of those solvents can be from 10 to 80% by weight, of the total weight.

Such oil additives are described, for example, in U.S. Pat. No. 4,834,908. They are especially preferred for the composition according to the invention. An especially preferred oil additive is known under the name MERGE®.

The compositions according to the invention are suitable for all methods of application that are customary in agriculture, for example pre-emergence application, post-emergence application and seed dressing. In the case of seed dressing, from 0.001 to 10 g of safener/kg of seed, preferably from 0.05 to 2 g of safener/kg of seed, are generally applied. When the safener is applied in liquid form shortly before sowing, with swelling of the seed, safener solutions are advantageously used that comprise the active ingredient in a concentration of from 1 to 10 000 ppm, preferably from 100 to 1000 ppm.

For application, the safeners of formula II or combinations of those safeners with the herbicides of formula I and, optionally the oil additives are advantageously processed, together with the adjuvants conventionally employed in formulation technology, into formulations, for example into emulsifiable concentrates, coatable pastes, directly sprayable or dilutable solutions, dilute emulsions, wettable powders, soluble powders, dusts, granules or microcapsules. Such formulations are described, for example, in WO 97/34485, on pages 9 to 13. The formulations are prepared in known manner, for example by intimately mixing and/or grinding the active ingredients with liquid or solid formulation adjuvants, for example solvents or solid carriers. Furthermore, surface-active compounds (surfactants) may also be used in preparation of the formulations. Solvents and solid carriers that are suitable for that purpose are mentioned, for example, in WO 97/34485 on page 6.

Suitable surface-active compounds are, depending on the nature of the active ingredient of formula I being formulated, non-ionic, cationic and/or anionic surfactants and mixtures of surfactants having good emulsifying, dispersing and wetting properties. Examples of suitable anionic, non-ionic and cationic surfactants are listed, for example, in WO 97/34485 on pages 7 and 8.

Furthermore, the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I–III, Chemical Publishing Co., New York, 1980–81, are also suitable for preparation of the herbicidal compositions according to the invention.

The herbicidal formulations generally comprise from 0.1 to 99% by weight, especially from 0.1 to 95% by weight, of active ingredient mixture comprising a compound of formula I together with a compound of formula II, from 0.01 to 2% by weight of oil additive, from 1 to 99.9% by weight of a solid or liquid formulation adjuvant and from 0 to 25% by weight, especially from 0.1 to 25% by weight, of a surfactant. Whereas commercial products will preferably be formulated as concentrates, the end user will normally employ dilute formulations.

The compositions may also comprise further ingredients such as stabilisers, for example vegetable oils or epoxidised vegetables oils (epoxidised coconut oil, rapeseed oil or soybean oil), antifoams, for example silicone oil, preservatives, viscosity regulators, binders and tackifiers, as well as fertilisers or other active ingredients. There are various suitable methods and techniques for using the safeners of formula II or compositions comprising them for protecting cultivated plants against the harmful effects of herbicides of formula I; the following are examples:

i) Seed dressing a) Dressing the seeds with a wettable powder formulation of a compound of formula II by shaking in a vessel until the formulation is uniformly distributed over the seed surface (dry dressing). Approximately from 1 to 500 g of compound of formula II (from 4 g to 2 kg of wettable powder) are used per 100 kg of seed.

b) Dressing the seeds with an emulsifiable concentrate of a compound of formula II according to method a) (wet dressing).

c) Dressing by immersing the seed in a liquid formulation comprising from 100 to 1000 ppm of a compound of formula II for from 1 to 72 hours and, if desired, subsequently drying the seeds (immersion dressing).

Dressing the seed or treating the germinated seedlings are naturally the preferred methods of application because the treatment with the active ingredient is directed wholly at the target crop. Generally from 1 to 1000 g of antidote, preferably from 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application in the form of a tank mixture

A liquid formulation of a mixture of antidote and herbicide (ratio of the one to the other from 10:1 to 1:100) is used, the rate of application of herbicide being from 0.005 to 5.0 kg per hectare. Such a tank mixture is applied before or after sowing.

iii) Application in the seed furrow

The compound of formula II is introduced into the open, sown seed furrow in the form of an emulsifiable concentrate, a wettable powder or granules and, after the seed furrow has been covered, the herbicide is applied pre-emergence in the normal manner.

iv) Controlled release of the active ingredient

The compound of formula II is applied in solution to granulated mineral carriers or polymerised granules (urea-formaldehyde) and dried. If desired, a coating may be applied (coated granules) which enables the active ingredient to be released in metered amounts over a predetermined period of time.

Preferred formulations have especially the following composition (%=percent by weight; 'active ingredient mixture' denotes the mixture of the compound of formula I with the compound of formula II)

| Emulsifiable concentrates: | |
|---|---|
| active ingredient mixture: | 1 to 90%, preferably 5 to 20% |
| surface-active agent: | 1 to 30%, preferably 10 to 20% |
| liquid carrier: | 5 to 94%, preferably 70 to 85% |
| Dusts: | |
| active ingredient mixture: | 0.1 to 10%, preferably 0.1 to 5% |
| solid carrier: | 99.9 to 90%, preferably 99.9 to 99% |
| Suspension concentrates: | |
| active ingredient mixture: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient mixture: | 0.5 to 90%, preferably 1 to 80% |
| surface-active agent: | 0.5 to 20%, preferably 1 to 15% |
| solid carrier: | 5 to 95%, preferably 15 to 90% |
| Granules: | |
| active ingredient mixture: | 0.1 to 30%, preferably 0.1 to 15% |
| solid carrier: | 99.5 to 70%, preferably 97 to 85% |

The Examples that follow illustrate the invention further. They do not limit the invention.

Formulation Examples for mixtures of herbicides of formula I and safeners of formula II (%=percent by weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyethylene glycol ether (36 mol of ethylene oxide) | 4% | — | 4% | 4% |
| octylphenoxypolyethylene glycol ether (7–8 mol of ethylene oxide) | — | 4% | — | 2% |
| cyclohexanone | — | — | 10% | 20% |
| aromatic $C_9$–$C_{12}$ hydrocarbon mixture | 85% | 78% | 55% | 16% |

Emulsions of any desired concentration can be prepared from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol (mol. wt. 400) | 20% | 10% | — | — |
| N-methyl-2-pyrrolidone | — | — | 30% | 10% |
| aromatic $C_9$–$C_{12}$ hydrocarbon mixture | 75% | 60% | — | — |

The solutions are suitable for application in the form of micro-drops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium disobutylnaphthalenesulfonate | — | 6% | 5% | 6% |
| octylphenoxypolyethylene glycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier material (Æ 0.1–1 mm) for example $CaCO_3$ or $SiO_2$ | 99.0% | 93% | 83% |

The active ingredient is dissolved in methylene chloride, the solution is sprayed onto the carrier, and the solvent is subsequently evaporated off in vacuo.

| F5. Coated granules | a) | b) | c) |
|---|---|---|---|
| active ingredient mixture | 0.1% | 5% | 15% |
| polyethylene glycol (mol. wt. 200) | 1.0% | 2% | 3% |
| highly dispersed silicic acid | 0.9% | 1% | 2% |
| inorganic carrier material (Æ 0.1–1 mm) for example $CaCO_3$ or $SiO_2$ | 98.0% | 92% | 80% |

The finely ground active ingredient is uniformly applied, in a mixer, to the carrier material moistened with polyethylene glycol, yielding non-dusty coated granules.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed with the adjuvants, and the mixture is ground, moistened with water, extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenoxypolyethylene glycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical to formulate the active ingredient of formula I and the mixing partner of formula II separately and then, shortly before application, to bring them together in the applicator in the desiring mixing ratio in the form of a "tank mixture" in water. The ability of the safeners of formula II to protect cultivated plants from the phytotoxic action of herbicides of formula I is illustrated in the following Examples.

Biological Examples

Examples B1, B2 and B3

Post-emergence applications of mixtures of a herbicide of formula I, wherein $R_1$ and $R_3$ are —$C_2H_5$; $R_4$ and $R_5$ together form a group $Z_z$ —$CR_{14}(R_{15})$—$CR_{16}(R_{17})$—O—$CR_{18}(R_{19})$—$CR_{20}(R_{21})$— ($Z_2$), wherein $R_{14}$, $R_{15}$, $R_{16}$, $R_{17}$, $R_{18}$, $R_{19}$, $R_{20}$ and $R_{21}$ are hydrogen; and G is either hydrogen (=herbicide no. $I_1$) or $(CH_3)_3CC(O)$— (=herbicide no $I_2$), with a safener of formula IIa, wherein $R_{22}$ is ethyl (=safener no. IIa$_1$), or of formula IIb, wherein $R_{23}$ is ethyl (=safener no. IIb$_1$), to wheat and barley, together with 3 different weeds. The test plants are grown in pots under greenhouse conditions until a post-application stage. A standard soil is used as the cultivation substrate. At a post-emergence stage, the herbicides, both alone and in admixture with safeners, are applied to the test plants or to cultivated plants of which the seeds were dressed with safeners. Application is carried out using an emulsion pre pared from a 25% emulsifiable concentrate (Example F1, b)) of the test substances using 500 l of water/ha. The rates of application are matched to the optimum dosages determined under field or greenhouse conditions. Evaluation of the tests is carried out after 9, 10, 20 and 24 days (100% action= complete destruction; 0% action=no phytotoxic action). The results obtained show that the safener used can significantly reduce the damage caused to the cultivated plants by the herbicide of formula I.

Examples of the action of the composition according to the invention are given in Tables B1, B2 and B3.

TABLE B1

Post-emergence application of herbicide no $I_1$, alone and in combination with safener no. $IIa_1$, to summer wheat, hard wheat and *Lolium rigidum*; evaluation 9 and 20 days after application.

| Plant | Evaluation [days] | Herbicide no. $I_1$ [a.i. g/ha] | | | Herbicide no. $I_1$ [a.i. g/ha] 500 + safener no. $IIa_1$ [a.i. g/ha] | | |
|---|---|---|---|---|---|---|---|
| | | 250 | 125 | 60 | 125 | 60 | 30 |
| summer wheat | 9 | 60 | 60 | 60 | 20 | 10 | 10 |
| hard wheat | 9 | 60 | 60 | 55 | 10 | 5 | 5 |
| summer wheat | 20 | 50 | 40 | 20 | 15 | 5 | 0 |
| hard wheat | 20 | 45 | 30 | 20 | 10 | 0 | 0 |
| *Lolium rigidum* | 20 | 100 | 100 | 95 | 100 | 95 | 95 |

TABLE B2

Post-emergence application of herbicide no. $I_1$ at concentrations of 125, 60, 30 and 15 g a.i./ha, alone and in combination with safener no. $IIa_1$ and $IIb_1$ at 30, 15, 8 and 4 g a.i./ha, to winter wheat and winter barley, and also *Agrostis spica-venti, Alopecurus myosuroides* and *Lolium rigidum*; evaluation 10 days after application.

| Plant | Herbicide no. $I_1$ [a.i. g/ha] | | | | Herbicide no. $I_1$ [a.i. g/ha] 125 60 30 15 + safener no. $IIa_1$ [a.i. g/ha] | | | | Herbicide no. $I_1$ [a.i. g/ha] 125 60 30 15 + safener no. $IIb_1$ [a.i. g/ha] | | | |
|---|---|---|---|---|---|---|---|---|---|---|---|---|
| | 125 | 60 | 30 | 15 | 30 | 15 | 8 | 4 | 30 | 15 | 8 | 4 |
| winter wheat | 20 | 10 | 5 | 0 | 0 | 0 | 0 | 0 | 10 | 5 | 0 | 0 |
| winter barley | 0 | 0 | 0 | 0 | 0 | 0 | 0 | 0 | 0 | 0 | 0 | 0 |
| *Agrostis* sp. | 80 | 80 | 70 | 70 | 80 | 80 | 70 | 60 | 80 | 80 | 70 | 70 |
| *Alopecurus* m. | 90 | 80 | 80 | 50 | 90 | 90 | 80 | 60 | 90 | 80 | 80 | 70 |
| *Lolium* r. | 80 | 60 | 60 | 60 | 80 | 80 | 70 | 60 | 80 | 80 | 70 | 60 |

TABLE B3

Post-emergence application of herbicide no. $I_2$ at concentrations of 125, 60, 30 and 15 g a.i./ha, alone and in combination with safener no. $IIa_1$ and $IIb_1$ at 30, 15, 8 and 4 g a.i./ha, to winter wheat and winter barley, and also *Agrostis spica-venti, Alopecurus myosuroides* and *Lolium rigidum*; evaluation 10 days and 24 days after application.

| Plant | Evaluation [days] | Herbicide no. $I_2$ [a.i. g/ha] | | | | Herbicide no. $I_2$ [a.i. g/ha] 125 60 30 15 + safener no. $IIa_1$ [a.i. g/ha] | | | | Herbicide no. $I_2$ [a.i. g/ha] 125 60 30 15 + safener no. $IIb_1$ [a.i. g/ha] | | | |
|---|---|---|---|---|---|---|---|---|---|---|---|---|---|
| | | 125 | 60 | 30 | 15 | 30 | 15 | 8 | 4 | 30 | 15 | 8 | 4 |
| winter wheat | 10 | 30 | 20 | 10 | 0 | 0 | 0 | 0 | 0 | 20 | 10 | 0 | 0 |
| winter barley | 10 | 10 | 0 | 0 | 0 | 0 | 0 | 0 | 0 | 0 | 0 | 0 | 0 |
| *Agrostis* sp. | 10 | 90 | 80 | 70 | 60 | 90 | 80 | 80 | 70 | 80 | 80 | 70 | 60 |
| *Alopecurus* m. | 10 | 90 | 80 | 80 | 60 | 90 | 80 | 70 | 40 | 90 | 80 | 60 | 50 |
| *Lolium* r. | 10 | 80 | 80 | 70 | 70 | 80 | 80 | 70 | 70 | 80 | 80 | 70 | 70 |
| winter wheat | 24 | 0 | 0 | 0 | 0 | 0 | 0 | 0 | 0 | 0 | 0 | 0 | 0 |
| winter barley | 24 | 0 | 0 | 0 | 0 | 0 | 0 | 0 | 0 | 0 | 0 | 0 | 0 |

The same results are obtained where the active ingredient mixture is formulated according to the other Formulation Examples mentioned above.

What is claimed is:

1. A selectively herbicidal composition which, in addition to customary inert formulation assistants, comprises as active ingredient a mixture of
   a) a herbicidally effective amount of a compound of formula I

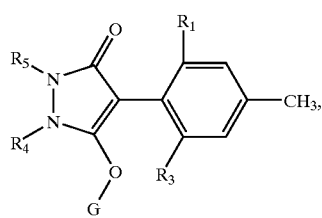

(I)

wherein $R_1$ and $R_3$ are, each independently of the other, ethyl, haloethyl, ethynyl, $C_1$- or $C_2$-alkoxy, $C_1$- or $C_2$-haloalkoxy, $C_1$- or $C_2$-alkylcarbonyl or $C_1$- or $C_2$-hydroxyalkyl;

$R_4$ and $R_5$ together are a group $Z_2$ which is $CR_{14}(R_{15})$—$CR_{16}(R_{17})$—O—$CR_{18}(R_{19})$—$CR_{20}(R_{21})$—;

$R_{14}$, $R_{15}$, $R_{16}$, $R_{17}$, $R_{18}$, $R_{19}$, $R_{20}$ and $R_{21}$ are, each independently of the others, hydrogen, halogen, $C_1$–$C_4$alkyl or $C_1$–$C_4$haloalkyl, wherein an alkylene ring may be fused or spiro-bound to the carbon atoms of the group $Z_2$, which alkylene ring, together with the carbon atoms of the group $Z_2$, to which it is bonded, contains from 2 to 6 carbon atoms and may be interrupted by oxygen, or the alkylene ring bridges at least one ring atom of the group $Z_2$;

G is hydrogen, —$C(X_1)$—$R_{30}$, —$C(X_2)$—$X_3$—$R_{31}$, —$C(X_4)$—$NR_{32}(R_{33})$, —$S(O)_2$—$R_{34}$, —$P(X_5)R_{35}R_{36}$, —$CH_2$—$X_6$—$R_{37}$ or an alkali metal, alkaline earth metal, sulfonium or ammonium cation;

$X_1$, $X_2$, $X_3$, $X_4$, $X_5$ and $X_6$ are, each independently of the others, oxygen or sulfur;

$R_{30}$, $R_{31}$, $R_{32}$, $R_{33}$, $R_{34}$, $R_{35}$, $R_{36}$ and $R_{37}$ are, each independently of the others, hydrogen, $C_1$–$C_{10}$alkyl, $C_1$–$C_{10}$haloalkyl, $C_1$–$C_{10}$cyanoalkyl, $C_1$–$C_{10}$nitroalkyl, $C_1$–$C_{10}$aminoalkyl, $C_2$–$C_5$-alkenyl, $C_2$–$C_5$haloalkenyl, $C_3$–$C_8$cycloalkyl, $C_1$–$C_5$alkylamino-$C_1$–$C_5$alkyl, di($C_1$–$C_5$alkyl)amino-$C_1$–$C_5$alkyl, $C_3$–$C_7$cycloalkyl-$C_1$–$C_5$alkyl, $C_1$–$C_5$alkoxy-$C_1$–$C_5$alkyl, $C_3$–$C_5$alkenyloxy-$C_1$–$C_5$alkyl, $C_3$–$C_5$alkynyloxy-$C_1$–$C_5$alkyl, $C_1$–$C_5$alkylthio-$C_1$–$C_5$alkyl, $C_1$–$C_5$alkylsulfoxy-$C_1$–$C_5$alkyl, $C_1$–$C_5$-alkylsulfonyl-$C_1$–$C_5$alkyl, $C_2$–$C_8$alkylideneaminooxy-$C_1$–$C_5$alkyl, $C_1$–$C_5$alkylcarbonyl-$C_1$–$C_5$alkyl, $C_1$–$C_5$alkoxycarbonyl-$C_1$–$C_5$alkyl, $C_1$–$C_5$alkylaminocarbonyl-$C_1$–$C_5$alkyl, di($C_1$–$C_5$alkyl)aminocarbonyl-$C_1$–$C_5$alkyl, $C_1$–$C_5$alkylcarbonylamino-$C_1$–$C_5$alkyl, $C_1$–$C_5$alkylcarbonyl-($C_1$–$C_5$-alkyl)-amino-$C_1$–$C_5$alkyl, tri($C_1$- or $C_2$-alkyl)silyl-$C_1$–$C_5$alkyl, phenyl, heteroaryl, phenyl-$C_1$–$C_5$alkyl, heteroaryl-$C_1$–$C_5$alkyl, phenoxy-$C_1$–$C_5$alkyl or heteroaryloxy-$C_1$–$C_5$alkyl, wherein the afore-mentioned aromatic rings may be substituted by halogen, nitro, cyano, amino, di($C_1$–$C_4$alkyl)amino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl;

$R_{34}$, $R_{35}$ and $R_{36}$ are, in addition, $C_1$–$C_{10}$alkoxy, $C_1$–$C_{10}$haloalkoxy, $C_1$–$C_5$alkylamino, di($C_1$–$C_5$-alkyl)amino, benzyloxy or phenoxy, wherein the aromatic rings of the last two substituents may be substituted by halogen, nitro, cyano, amino, dimethylamino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl; and $R_{37}$ is, in addition, $C_1$–$C_{10}$alkylcarbonyl, or a salt or diastereoisomer of a compound of formula I, and b) an amount, which is effective for antagonism of the herbicide, of a safener of formula IIa

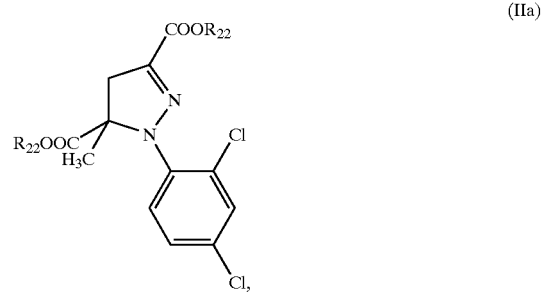

(IIa)

wherein $R_{22}$ is hydrogen, or an alkali metal, alkaline earth metal, sulfonium or ammonium cation, or ethyl.

2. A composition according to claim 1, which comprises as active ingredient a mixture of a) a herbicidally effective amount of a herbicide of formula I, wherein $R_1$, $R_3$, $R_4$, $R_5$ and G are as defined in claim 1, and b) an amount, which is effective for antagonism of the herbicide, of a safener of formula IIa, wherein $R_{22}$ is as defined in claim 1 for formula IIa.

3. A composition according to claim 1, wherein $R_1$ and $R_3$ in the compounds of formula I are, each independently of the other, ethyl, haloethyl, ethynyl, $C_1$- or $C_2$-alkoxy or $C_1$- or $C_2$-haloalkoxy.

4. A composition according to claim 1, wherein $R_4$ and $R_5$ in the compounds of formula I together form a group $Z_2$ which is —$CR_{14}(R_{15})$—$CR_{16}(R_{17})$—O—$CR_{18}(R_{19})$—$CR_{20}(R_{21})$—, wherein $R_{14}$, $R_{15}$, $R_{16}$, $R_{17}$, $R_{18}$, $R_{19}$, $R_{20}$ and $R_{21}$ are hydrogen.

5. A composition according to claim 1, wherein G in the compounds of formula I is hydrogen, —$C(X_1)$—$R_{30}$, —$C(X_2)$—$X_3$—$R_{31}$, —$C(X_4)$—$NR_{32}(R_{33})$, —$S(O)_2$—$R_{34}$, —$P(X_5)R_{35}R_{36}$, —$CH_2$—$X_6$—$R_{37}$ or an alkali metal, alkaline earth metal, sulfonium or ammonium cation; $X_1$, $X_2$, $X_3$, $X_4$, $X_5$ and $X_6$ are, each independently of the others, oxygen or sulfur; $R_{30}$, $R_{31}$, $R_{32}$, $R_{33}$, $R_{34}$, $R_{35}$, $R_{36}$ and $R_{37}$ are, each independently of the others, hydrogen, $C_1$–$C_8$alkyl, $C_1$–$C_8$haloalkyl, $C_1$–$C_8$cyanoalkyl, $C_1$–$C_8$nitroalkyl, $C_1$–$C_8$aminoalkyl, $C_2$–$C_5$-alkenyl, $C_2$–$C_5$haloalkenyl, $C_3$–$C_8$cycloalkyl, $C_1$–$C_5$alkylamino-$C_1$–$C_2$alkyl, di($C_1$–$C_5$alkyl)amino-$C_1$–$C_2$alkyl, $C_3$–$C_7$cycloalkyl-$C_1$–$C_2$alkyl, $C_1$–$C_4$alkoxy-$C_1$–$C_4$alkyl, $C_2$–$C_4$alkenyloxy-$C_1$–$C_4$alkyl, $C_3$–$C_4$alkynyloxy-$C_1$–$C_4$alkyl, $C_1$–$C_4$alkylthio-$C_1$–$C_4$alkyl, $C_1$–$C_4$alkylsulfoxy-$C_1$–$C_2$alkyl, $C_1$–$C_2$-alkylsulfonyl-$C_1$–$C_2$alkyl, $C_2$–$C_8$alkylideneaminooxy-$C_1$–$C_2$-alkyl, $C_1$–$C_5$alkylcarbonyl-$C_1$–$C_2$alkyl, $C_1$–$C_5$alkoxycarbonyl-$C_1$–$C_2$alkyl, $C_1$–$C_5$alkylaminocarbonyl-$C_1$–$C_2$alkyl, di($C_1$–$C_4$alkyl)aminocarbonyl-$C_1$–$C_2$alkyl, $C_1$–$C_5$alkylcarbonylamino-$C_1$–$C_2$alkyl, $C_1$–$C_5$alkylcarbonyl-($C_1$–$C_3$alkyl)-amino-$C_1$–$C_2$alkyl, tri ($C_1$- or $C_2$-alkyl)silyl-$C_1$–$C_3$-alkyl, phenyl, heteroaryl, phenyl-$C_1$–$C_2$alkyl, heteroaryl-$C_1$–$C_2$alkyl, phenoxy-$C_1$–$C_2$alkyl or heteroaryloxy-$C_1$–$C_2$alkyl; $R_{34}$, $R_{35}$ and $R_{36}$ are, in addition, $C_1$–$C_6$alkoxy, $C_1$–$C_6$haloalkoxy, $C_1$–$C_3$alkylamino, di($C_1$–$C_3$-alkyl)amino, benzyloxy or phenoxy, wherein the aromatic rings of the last two substituents may be substituted by halogen, nitro, cyano, amino, dimethylamino, hydroxy, methoxy, ethoxy, methylthio, ethylthio, formyl, acetyl, propionyl, carboxyl, $C_1$–$C_5$alkoxycarbonyl or by $C_1$- or $C_2$-haloalkyl; and $R_{37}$ is, in addition, $C_1$–$C_8$alkylcarbonyl.

6. A composition according to claim 5, wherein G is hydrogen, —C($X_1$)—$R_{30}$, —C($X_2$)—$X_3$—$R_{31}$, —C($X_4$)—NR$_{32}$($R_{33}$), —S(O)$_2$—$R_{34}$, —P($X_5$)$R_{35}R_{36}$, —CH$_2$—$X_6$—$R_{37}$ or an alkali metal, alkaline earth metal, sulfonium or ammonium cation; $X_1$, $X_2$, $X_3$, $X_4$, $X_5$ and $X_6$ are, each independently of the others, oxygen or sulfur; $R_{30}$, $R_{31}$, $R_{32}$, $R_{33}$, $R_{34}$, $R_{35}$, $R_{36}$ and $R_{37}$ are, each independently of the others, hydrogen, $C_1$–$C_8$alkyl, $C_1$–$C_8$haloalkyl, $C_2$–$C_5$alkenyl, $C_2$–$C_5$haloalkenyl, $C_3$–$C_8$-cycloalkyl, $C_3$–$C_7$cycloalkyl-$C_1$–$C_2$alkyl, $C_1$–$C_4$alkoxy-$C_1$–$C_4$alkyl, phenyl, heteroaryl, phenyl-$C_1$–$C_2$alkyl, heteroaryl-$C_1$–$C_2$alkyl, phenoxy-$C_1$–$C_2$alkyl or heteroaryloxy-$C_1$–$C_2$alkyl, $R_{34}$, $R_{35}$ and $R_{36}$ are, in addition, $C_1$–$C_6$alkoxy, $C_1$–$C_3$alkylamino or di($C_1$–$C_3$-alkyl)amino; and $R_{37}$ is, in addition, $C_1$–$C_8$alkylcarbonyl.

7. A method of selectively controlling weeds and grasses in crops of useful plants, which comprises treating the useful plants, their seeds or seedlings or the crop area thereof with, simultaneously or separately, a) a herbicidally effective amount of a herbicide of formula I as claimed in claim 1, b) an amount, which is effective for antagonism of the herbicide, of a safener of formula IIa and, optionally, c) an additive comprising an oil of vegetable origin or an alkylated derivative thereof, or a mineral oil or a mixture thereof.

8. A method according to claim 7, which comprises treating crops of useful plants or crop areas for crops of useful plants with from 0.001 to 2 kg/ha of a herbicide of formula I and an amount of from 0.001 to 0.5 kg/ha of a safener of formula IIa.

9. A method according to claim 7, wherein the crops of useful plants are cereals, maize and sorghum.

10. A composition according to claim 1, which also comprises, in addition to the formulation adjuvants, an oil additive in the form of a vegetable oil concentrate consisting of the 4 components (A) from 20 to 90% by weight of an alkyl ester of a higher fatty acid ($C_4$–$C_{22}$), (B) from 4 to 40% by weight of an anionic surfactant, (C) from 2 to 20% by weight of a higher fatty acid ($C_{10}$–$C_{20}$), and (D) up to 140% by weight, based on the total amount of components (A) to (C), of a hydrocarbon.

11. A composition according to claim 10, wherein (A) is a $C_1$–$C_4$alkyl ester of a $C_{12}$–$C_{18}$ fatty acid, (B) is an anionic surfactant of the dodecylbenzylsulfonate type, (C) is a $C_{12}$–$C_{18}$ fatty acid, and (D) is an aromatic hydrocarbon.

* * * * *

UNITED STATES PATENT AND TRADEMARK OFFICE
CERTIFICATE OF CORRECTION

| | |
|---|---|
| PATENT NO. | : 6,962,894 B2 |
| APPLICATION NO. | : 09/730559 |
| DATED | : November 8, 2005 |
| INVENTOR(S) | : Tetsuyoshi Ishiwata et al. |

It is certified that error appears in the above-identified patent and that said Letters Patent is hereby corrected as shown below:

Title page,
Item [56], References Cited, OTHER PUBLICATIONS,
"Genbank entry M58511," reference, "iron-respnsive" should read
-- iron-responsive --; and "Plant, Physiol," should read -- Plant Physiol, --;
"Lai Kar Neng, et al.," reference, "factor-βin" should read -- factor-B in --;
"International ," should read -- International, --; and
"Ichinose, et al.," reference, "crytokine" should read -- cytokine --.

Column 6,
Line 33, "Biotechnology," should read -- Biotechnology, --.

Column 10,
Line 2, "*Brevibacterium flavunm*" should read -- *Brevibacterium flavum* --; and
Line 24, "MF a1 promoter" should read -- MF α1 promoter --.

Column 12,
Line 47, "by" should read -- be --.

Column 20,
Line 29, "DNTP" should read -- dNTP --;
Line 30, "(DATP," should read -- (dATP, --; and
Line 42, "DNTP," should read -- dNTP, --.

Column 21,
Line 22, "DNTP," should read -- dNTP, --.

Column 23,
Line 59, "5"-RACE" should read -- 5'-RACE --.

Column 26,
Line 25, "DNTP" should read -- dNTP --.

Column 28,
Line 27, "INP303A phi-3" should read -- INP303A ph1-3 --.

Column 31,
Line 20, "to" should read -- to be --.

Column 34,
Line 66, "and" (second occurrence) should be deleted.

UNITED STATES PATENT AND TRADEMARK OFFICE
CERTIFICATE OF CORRECTION

PATENT NO. : 6,962,894 B2
APPLICATION NO. : 09/730559
DATED : November 8, 2005
INVENTOR(S) : Tetsuyoshi Ishiwata et al.

It is certified that error appears in the above-identified patent and that said Letters Patent is hereby corrected as shown below:

Column 38,
Line 39, "be" should be deleted; and
Line 64, "of" should be deleted.

Column 112,
Line 4, "form" should read -- from --; and
Line 9, "healthy" should read -- a healthy --.

Signed and Sealed this

Twenty-seventh Day of June, 2006

JON W. DUDAS
*Director of the United States Patent and Trademark Office*

UNITED STATES PATENT AND TRADEMARK OFFICE
CERTIFICATE OF CORRECTION

PATENT NO.         : 6,962,894 B1
APPLICATION NO. : 10/070766
DATED              : November 8, 2005
INVENTOR(S)        : Jutta Glock It is certified that error appears in the above-identified patent and that said Letters Patent is hereby corrected as shown below:

This certificate supersedes certificate of correction issued June 27, 2006, the number was erroneously mentioned and should be vacated since no certificate of correction was granted for this patent number.

Signed and Sealed this

Fifth Day of September, 2006

JON W. DUDAS
*Director of the United States Patent and Trademark Office*